United States Patent
Weitz et al.

(10) Patent No.: US 9,186,346 B2
(45) Date of Patent: Nov. 17, 2015

(54) METHODS FOR REDUCING THE RISK OF AN ADVERSE TERIFLUNOMIDE AND ROSUVASTATIN INTERACTION IN MULTIPLE SCLEROSIS PATIENTS

(71) Applicants: Dietmar Weitz, Konigstein im Taunus (DE); Francoise Menguy-Vacheron, Paris (FR); Pierre-Francois Clot, Epinay sur Orge (FR); Sandrine Turpault, Pennington, NJ (US)

(72) Inventors: Dietmar Weitz, Konigstein im Taunus (DE); Francoise Menguy-Vacheron, Paris (FR); Pierre-Francois Clot, Epinay sur Orge (FR); Sandrine Turpault, Pennington, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/172,082

(22) Filed: Feb. 4, 2014

(65) Prior Publication Data
US 2014/0256758 A1   Sep. 11, 2014

Related U.S. Application Data

(60) Provisional application No. 61/777,361, filed on Mar. 12, 2013.

(30) Foreign Application Priority Data

Feb. 4, 2013   (EP) ..................... 13305130

(51) Int. Cl.
*A61K 31/275*   (2006.01)
*A61K 31/505*   (2006.01)
*A61K 31/277*   (2006.01)

(52) U.S. Cl.
CPC ............. *A61K 31/277* (2013.01); *A61K 31/505* (2013.01)

(58) Field of Classification Search
CPC    A61K 2300/00; A61K 31/277; A61K 31/505
USPC .......................... 514/256, 275, 521, 557, 627
See application file for complete search history.

(56) References Cited

U.S. PATENT DOCUMENTS

| 4,598,072 | A | * | 7/1986 | Schweikert et al. ........... 514/170 |
| 4,658,957 | A | * | 4/1987 | Guth et al. .................... 206/365 |
| 5,679,709 | A |   | 10/1997 | Bartlett et al. |
| 6,794,410 | B2 |   | 9/2004 | Wettstein |
| 2004/0013643 | A1 | * | 1/2004 | Mach .......................... 424/85.6 |

FOREIGN PATENT DOCUMENTS

EP    1935416 A2 *  6/2008  ........... A61K 31/165

OTHER PUBLICATIONS

O'Connor et al.; "A Phase II study of the safety and efficacy of teriflunomide in multiple sclerosis with relapses"; Mar. 2006; Neurology; vol. 66, No. 6; pp. 894-900.*
Creator, Prescribing information (2010), pp. 1-43.
Weitz, et al., Teriflunomide: Potential for Transporter Mediated Drug-Drug Interactions, Nature, vol. 93, Supplement 1, (2013), PIII-72, pp. S112-S113.

* cited by examiner

*Primary Examiner* — My-Chau T Tran
(74) *Attorney, Agent, or Firm* — Jiang Lin

(57) ABSTRACT

This invention relates to a method for managing the risk of an adverse interaction between teriflunomide and a substrate of breast cancer resistance protein (BCRP) and/or organic anion transporting polypeptide B1 and B3 (OATP1B1/B3).

8 Claims, 1 Drawing Sheet

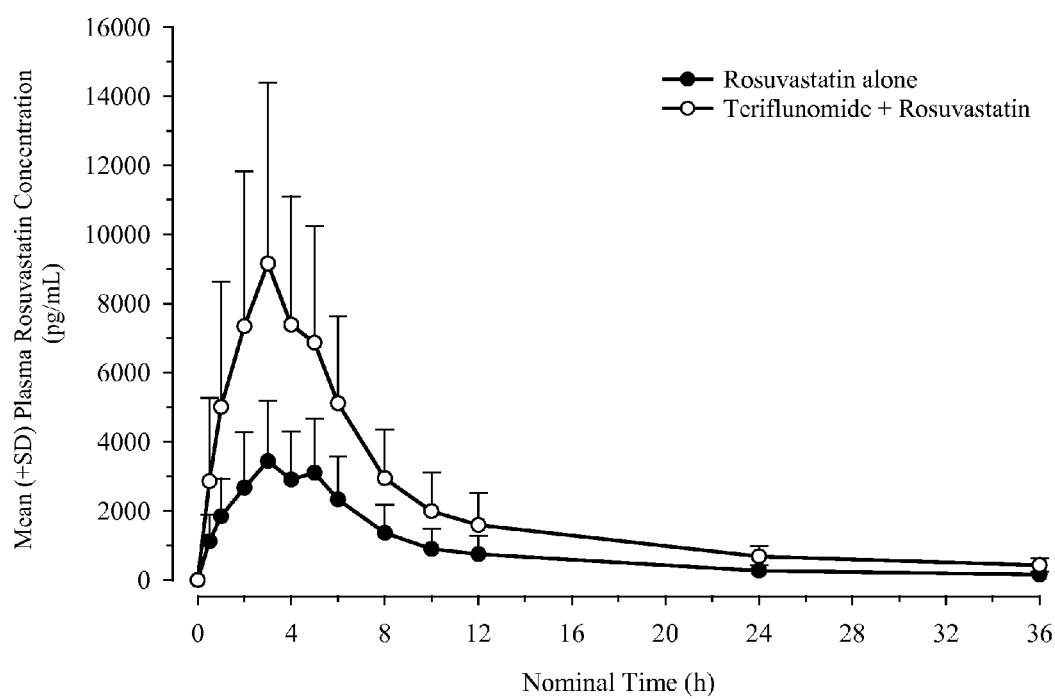

METHODS FOR REDUCING THE RISK OF AN ADVERSE TERIFLUNOMIDE AND ROSUVASTATIN INTERACTION IN MULTIPLE SCLEROSIS PATIENTS

This application claims priority of European Patent Application No. 13305130, filed Feb. 4, 2013. This application also claims benefit of Provisional Application No. 61/777,361, filed Mar. 12, 2013. Both applications are incorporated by reference in their entireties.

FIELD OF THE INVENTION

This invention relates to a method for managing the risk of an adverse interaction between teriflunomide and a substrate of breast cancer resistance protein (BCRP) and/or organic anion transporting polypeptide B1 and B3 (OATP1B1/B3).

BACKGROUND OF THE INVENTION

Teriflunomide is a novel oral disease-modifying therapy (DMT) for the treatment of relapsing forms of multiple sclerosis (RMS). Teriflunomide blocks de novo pyrimidine synthesis, which inhibits the replication and function of activated (but not resting) lymphocytes.

The compound of (Z)-2-cyano-3-hydroxy-but-2-enoic acid-(4'-trifluoromethylphenyl)-amide (also known as teriflunomide, Formula I) is described in U.S. Pat. No. 5,679,709.

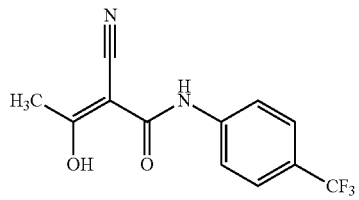

I

The use of teriflunomide for treating multiple sclerosis is described in U.S. Pat. No. 6,794,410. In vitro, teriflunomide inhibits of human OATP1B1 with a half maximal inhibitory concentration ($IC_{50}$) of 7.1 µM, OATP1B3 with an $IC_{50}$ of 7.04 µM, OAT3 with an $IC_{50}$ of 1.3 µM and BCRP with an $IC_{50}$ of 0.15 µM.

Rosuvastatin, a hypocholesterolemiant drug, is a selective, reversible, competitive inhibitor of 3-hydroxy-3-methylglutarylcoenzyme A (HMG-CoA) reductase, the rate-limiting enzyme that converts HMG-CoA to mevalonate early in the cholesterol pathway. Rosuvastatin is a substrate for NTCP, OATP1B1, OATPB1B3, organic anion transporter 3 (OAT3) and BCRP transporters.

During an interaction study with teriflunomide, it is now found that administration of this active principle together with rosuvastatin causes an increase in the plasma concentration of rosuvastatin.

SUMMARY OF THE INVENTION

Accordingly, this invention relates to a method for managing the risk of teriflunomide and rosuvastatin interaction in a patient having multiple sclerosis, particularly relapsing forms of multiple sclerosis, wherein rosuvastatin is co-administered with teriflunomide, comprising administering to the patient about 7 or 14 mg of teriflunomide daily, and administering to the patient rosuvastatin which is at the amount of about 50% of the normal dose of rosuvastatin.

BRIEF DESCRIPTION OF THE DRAWINGS

FIG. 1 shows plasma concentration of rosuvastatin following administration of rosuvastatin alone (Day 1) or with teriflunomide (Day 12) (n≤15).

DETAILED DESCRIPTION OF THE INVENTION

As used above, and throughout the description of the invention, the following terms, unless otherwise indicated, shall be understood to have the following meanings:

"Administering a combination of teriflunomide and rosuvastatin" means administering both teriflunomide and rosuvastatin at the same time, in the same day or within a period of 24 hours, particularly within a period of 12 hours.

"Co-administered" and "co-administering" means being administered or administering at the same time, in the same day or within a period of 24 hours, particularly within a period of 12 hours.

"Normal dose of rosuvastatin" means a dose of rosuvastatin that would be recommended for a patient to take or a doctor would prescribe the patient to take if the patient is not taking teriflunomide concurrently. In one aspect, the normal dose of rosuvastatin is the dose approved by U.S. Food and Drug Administration, which is 5-40 mg daily. In another aspect, the normal dose of rosuvastatin is a dose that a patient has been taking prior to the initiation of the treatment with teriflunomide. The dose of rosuvastatin is calculated based on its free acid form. It should be understood that rosuvastatin can be administered as a pharmaceutically acceptable salt, particularly as rosuvastatin calcium, and the amount of salt administered should be adjusted accordingly.

"Patient" means a human.

"Pharmaceutically acceptable salts" as used herein means that the salts of the compound of the present invention can be used in medicinal preparations.

The present invention also relates to a method of providing teriflunomide wherein the teriflunomide is provided along with information indicating that it is useful for treating patients with multiple sclerosis, particularly relapsing forms of multiple sclerosis, and in cases said patients also receive treatment of rosuvastatin wherein rosuvastatin is co-administered with teriflunomide, reducing the normal dose of rosuvastatin by about 50% is recommended.

The present invention also relates to a method of promoting the use of teriflunomide comprising conveying to a recipient at least one message comprising teriflunomide is useful for treating multiple sclerosis, particularly relapsing forms of multiple sclerosis, and in cases said patients also receive treatment of rosuvastatin wherein rosuvastatin is co-administered with teriflunomide, reducing the normal dose of rosuvastatin by about 50% is recommended.

The present invention also relates to an article of manufacture comprising
a) a packaging material:
b) teriflunomide, and
c) a label or package insert contained within the packaging material indicating that teriflunomide is useful for treating multiple sclerosis, particularly relapsing forms of multiple sclerosis, and in cases said patients also receive treatment of rosuvastatin wherein rosuvastatin is co-administered with teriflunomide, reducing the normal dose of rosuvastatin by about 50% is recommended.

The present invention also relates to a package comprising teriflunomide and a label, said label comprising a printed statement which informs a prospective user that:
a) teriflunomide is indicated in patients with relapsing forms of multiple sclerosis; and
b) in cases said patients also receive treatment of rosuvastatin wherein rosuvastatin is co-administered with teriflunomide, reducing the normal dose of rosuvastatin by about 50% is recommended.

The present invention also relates to a method for administering a combination of teriflunomide and rosuvastatin to a patient having multiple sclerosis, particularly relapsing forms of multiple sclerosis, comprising administering to the patient about 7 or 14 mg of teriflunomide daily, and co-administering to the patient rosuvastatin which is at the amount of about 50% of the normal dose of rosuvastatin.

The present invention may be better understood by reference to the following non-limiting Example, which is exemplary of the invention. It should in no way be construed, however, as limiting the breath of the scope of the invention.

EXAMPLE

A single-center, open-label, 1-sequence, 2-period, 2-treatment crossover study with a 5-day washout between periods was conducted in 15 healthy male subjects aged 18 to 45 to evaluate the effect of repeated doses of teriflunomide on the pharmacokinetics (PK) of a single dose of rosuvastatin 10 mg. All subjects received the following treatments during each period:
1. Period 1: A single 10 mg dose of rosuvastatin was administered in fasted state followed by a 5-day washout (from Days 1 to 6). Day 6 corresponded to Day 1 of Period 2.
2. Period 2: A loading dose of 70 mg teriflunomide was administered once a day for 4 days (Days 1 to 4), followed by 14 mg once a day for 8 days (Days 5 to 12) in fed conditions except for Day 12. A single dose of 10 mg rosuvastatin was co-administered with teriflunomide on Day 12 in fasted conditions.

After last PK sample for rosuvastatin in Period 2 and discharge, cholestyramine was administered for at least 11 days in order to accelerate the elimination of teriflunomide and until teriflunomide concentration was ≤25 µg/mL.

The total duration of study participation for each subject was up to 3 months, including the screening period and the cholestyramine washout procedure up to the end-of-study (EOS) visit.
1. Screening: −21 to −1 days before inclusion
2. Period 1: 5 days (from Days 1 to 6)
3. Period 2: 13 days+11 days of cholestyramine treatment (24 days)

The EOS visit (Day 35 to 42) was not complete until the subject's teriflunomide concentration was 0.25 µg/mL or lower.

Criteria for Evaluation:
The following PK parameters were calculated using non-compartmental methods from plasma rosuvastatin concentration obtained after single dose administration:
Primary:
Rosuvastatin: Area under the plasma concentration versus time curve (AUC) from time zero to the real time corresponding to the last concentration above the lower limit of quantitation, $t_{last}$, ($AUC_{last}$) and area under the plasma concentration versus time curve extrapolated to infinity (AUC).

Secondary:
Rosuvastatin: Maximum plasma concentration ($C_{max}$) observed, time to reach maximum concentration ($T_{max}$), $t_{last}$, and terminal half-life ($t_{1/2z}$).
Teriflunomide: Plasma concentration before treatment administration on Days 10 to 13 during repeated dosing and plasma concentration during cholestyramine treatment on Days 14, 15, 16, 20 and 25.

Pharmacokinetic sampling times and bioanalytical methods:
Sampling:
Rosuvastatin: Blood samples were collected at predose, 0.5, 1, 2, 3, 4, 5, 6, 8, 10, 12, 24 and 36 hours postdose on Day 1 of Period 1 and Day 12 of Period 2.
Teriflunomide: Blood samples were collected at predose on Days 10, 11, 12, 13, 14, 15, 16, 20 and 25 in Period 2.

Bioanalytical Methods:
Rosuvastatin plasma concentrations were determined by a validated liquid chromatography couples with tandem mass spectrometry (LC-MS/MS) method, with a LLOQ (lower limit of quantification) of 50.1 pg/mL. Teriflunomide plasma concentrations were determined with a validated LC-MS/MS method with an LLOQ of 0.01 µg/mL.

Statistical Analysis:
Rosuvastatin PK parameters and teriflunomide $C_{trough}$ (trough plasma concentration) were summarized with descriptive statistics for each treatment. For log transformed $C_{max}$, $AUC_{last}$ and AUC of rosuvastatin, the effect of repeated oral doses of teriflunomide on single-dose rosuvastatin PK parameters was analyzed using a linear mixed-effect model to obtain estimates and 90% confidence intervals (CIs) for the ratio of geometric means of rosuvastatin co-administered with teriflunomide versus rosuvastatin alone.

Results:
It was found that there was an increase in mean rosuvastatin $C_{max}$ and AUC (2.65- and 2.51-fold, respectively), following teriflunomide 70 mg QD for 4 days and 14 mg QD for 8 days. Mean±SD (CV %) [Geometric Mean] of the pharmacokinetic parameters of rosuvastatin with ratio estimates and 90% CIs are shown in Table I below and FIG. 1.

|  | Rosuvastatin alone | Rosuvastatin + Teriflunomide | Treatment Ratio [a] (90% CI) |
|---|---|---|---|
| N | 15 | 14 | — |
| $C_{max}$ (pg/mL) | 3650 ± 1780 | 9340 ± 5110 | 2.65 (2.25, 3.12) |
| $t_{max}$ [b] (h) | 3.00 (2.00-5.00) | 3.00 (2.00-3.00) | — |
| $t_{1/2z}$ (h) | 11.1 ± 2.99 | 12.3 ± 2.28 | — |
| $AUC_{last}$ (pg · h/mL) [c] | 31500 ± 16400 | 75400 ± 38700 | 2.52 (2.17, 2.91) |
| AUC (pg · h/mL) | 34800 ± 17300 [d] | 83000 ± 41400 | 2.51 (2.16, 2.91) |

[a] Teriflunomide + rosuvastatin versus rosuvastatin alone;
[b] Median (min-Max);
[c] Median $t_{last}$ was 36 h for both treatment;
[d] n = 14 due to AUC extrapolation >20%

CONCLUSION

Teriflunomide is an inhibitor of BCRP and an OATP1B1/B3 substrate. Therefore, a 50% dose reduction of rosuvastatin is recommended when co-administering with teriflunomide. For other substrates of BCRP (e.g. methotrexate, topotecan, sulfasalazine, daunorubicin, doxorubicin) and the OATP family, especially HMG-Co reductase inhibitors (e.g. simvastatin, atorvastatin pravastatin, methotrexate, nateglinide, repaglinide, rifampin), concomitant administration of teriflunomide should also be undertaken with caution. Patients should be monitored closely for signs and symptoms of excessive exposure to the drugs and reduction of the dose of these drugs should be considered.

We claim:

1. A method for treating multiple sclerosis while managing the risk of teriflunomide and rosuvastatin interaction in a patient having multiple sclerosis, wherein rosuvastatin is co-administered with teriflunomide, comprising administering to the patient about 7 or 14 mg of teriflunomide daily, and administering to the patient rosuvastatin which is at the amount of about 50% of the normal dose of rosuvastatin.

2. The method according to claim 1, wherein the patient has relapsing forms of multiple sclerosis.

3. The method according to claim 1, wherein rosuvastatin is co-administered with teriflunomide at the same time.

4. The method according to claim 2, wherein rosuvastatin is co-administered with teriflunomide at the same time.

5. A method for treating multiple sclerosis while managing the risk of teriflunomide and rosuvastatin interaction in a patient having multiple sclerosis, wherein rosuvastatin is co-administered with teriflunomide, comprising administering to the patient about 7 or 14 mg of teriflunomide daily, and administering to the patient rosuvastatin at a dose that does not exceed 10 mg once daily.

6. The method according to claim 5, wherein the patient has relapsing forms of multiple sclerosis.

7. The method according to claim 5, wherein rosuvastatin is co-administered with teriflunomide at the same time.

8. The method according to claim 6, wherein rosuvastatin is co-administered with teriflunomide at the same time.

* * * * *

UNITED STATES PATENT AND TRADEMARK OFFICE
CERTIFICATE OF CORRECTION

| | |
|---|---|
| PATENT NO. | : 9,186,346 B2 |
| APPLICATION NO. | : 14/172082 |
| DATED | : November 17, 2015 |
| INVENTOR(S) | : Dietmar Weitz et al. |

It is certified that error appears in the above-identified patent and that said Letters Patent is hereby corrected as shown below:

On title page, item (56), under "Other Publications", in column 2, line 4, delete "Creator," and insert -- Crestor, --, therefor.

In the Drawings:

On Sheet 1 of 1, Y-axis in Figure 1, line 1, delete "Mcan" and insert -- Mean --, therefor.

On Sheet 1 of 1, Y-axis in Figure 1, line 1, delete "Conccntration" and insert -- Concentration --, therefor.

On Sheet 1 of 1, in Figure 1, line 2, delete "Tcriflunomidc" and insert -- Teriflunomide --, therefor.

Signed and Sealed this
Fifth Day of April, 2016

Michelle K. Lee
*Director of the United States Patent and Trademark Office*

UNITED STATES PATENT AND TRADEMARK OFFICE
CERTIFICATE OF CORRECTION

PATENT NO. : 9,186,346 B2  
APPLICATION NO. : 14/172082  
DATED : November 17, 2015  
INVENTOR(S) : Dietmar Weitz et al.

Page 1 of 1

It is certified that error appears in the above-identified patent and that said Letters Patent is hereby corrected as shown below:

In the specification,

In column 1, line 28, delete "-(4'-trifluoromethylphenyI)-" and insert -- -(4'-trifluoromethylphenyl)- --, therefor.

Signed and Sealed this  
Second Day of August, 2016

Michelle K. Lee  
*Director of the United States Patent and Trademark Office*